United States Patent [19]
Kluger

[11] Patent Number: 4,957,495
[45] Date of Patent: Sep. 18, 1990

[54] DEVICE FOR SETTING THE SPINAL COLUMN

[76] Inventor: Patrick Kluger, Fichtenstr. 5, D-3590 Bad Wildungen-Reinhardshausen, Fed. Rep. of Germany

[21] Appl. No.: 290,104
[22] PCT Filed: Mar. 31, 1988
[86] PCT No.: PCT/DE88/00208
§ 371 Date: Dec. 1, 1988
§ 102(e) Date: Dec. 1, 1988
[87] PCT Pub. No.: WO88/07357
PCT Pub. Date: Oct. 6, 1988

[30] Foreign Application Priority Data
Apr. 1, 1987 [DE] Fed. Rep. of Germany ....... 3711091

[51] Int. Cl.$^5$ .............................................. A61B 17/60
[52] U.S. Cl. ........................................ 606/58; 606/57; 606/59; 606/61; 128/69
[58] Field of Search ............ 128/92 YM, 92 YJ, 92 Z, 128/92 ZZ, 92 ZY, 92 ZW, 69–74, 88, 92 ZK; 606/54, 55, 57–59, 72, 73, 61

[56] References Cited

U.S. PATENT DOCUMENTS

| | | | |
|---|---|---|---|
| 2,238,870 | 4/1941 | Haynes | 128/84 R |
| 2,439,995 | 4/1948 | Thrailkill | 128/84 R |
| 4,548,199 | 10/1985 | Agee | 128/92 ZK |
| 4,572,170 | 2/1986 | Cronk et al. | 128/88 X |
| 4,573,455 | 3/1986 | Hoy | 128/88 X |
| 4,611,586 | 9/1986 | Agee et al. | 128/92 ZK |
| 4,733,657 | 3/1988 | Kluger | 128/92 YM |

FOREIGN PATENT DOCUMENTS

| | | | |
|---|---|---|---|
| 2615095 | 11/1988 | France | 128/69 |
| 1017311 | 5/1983 | U.S.S.R. | 128/92 Z |
| 1084017 | 4/1984 | U.S.S.R. | 128/92 YM |

OTHER PUBLICATIONS

Kluger, Gerner; Mechanik des Fixateur, 1986.

Primary Examiner—Robert A. Hafer
Assistant Examiner—Kevin G. Rooney
Attorney, Agent, or Firm—Collard, Roe & Galgano

[57] ABSTRACT

A device for adjusting a vertebral column with damaged vertebrae comprises an adjustable arm on a guiding axis and a stationary arm attached to the guiding axis, each arm having a hollow receiving body adjustable in two planes for a lengthening rod, which can be connected with a tire-fond. Each arm (2, 4) has an intermediate jointed piece (5, 5a) with an intermediate jointed piece (5, 5a) with two joints (6, 7), each intermediate jointed piece (5, 5a) being connected in a hinged manner to a support (8) for the hollow receiving body which is designed as an attachable cylindrical piece (15) with a tangential drilled hole (16).

13 Claims, 4 Drawing Sheets

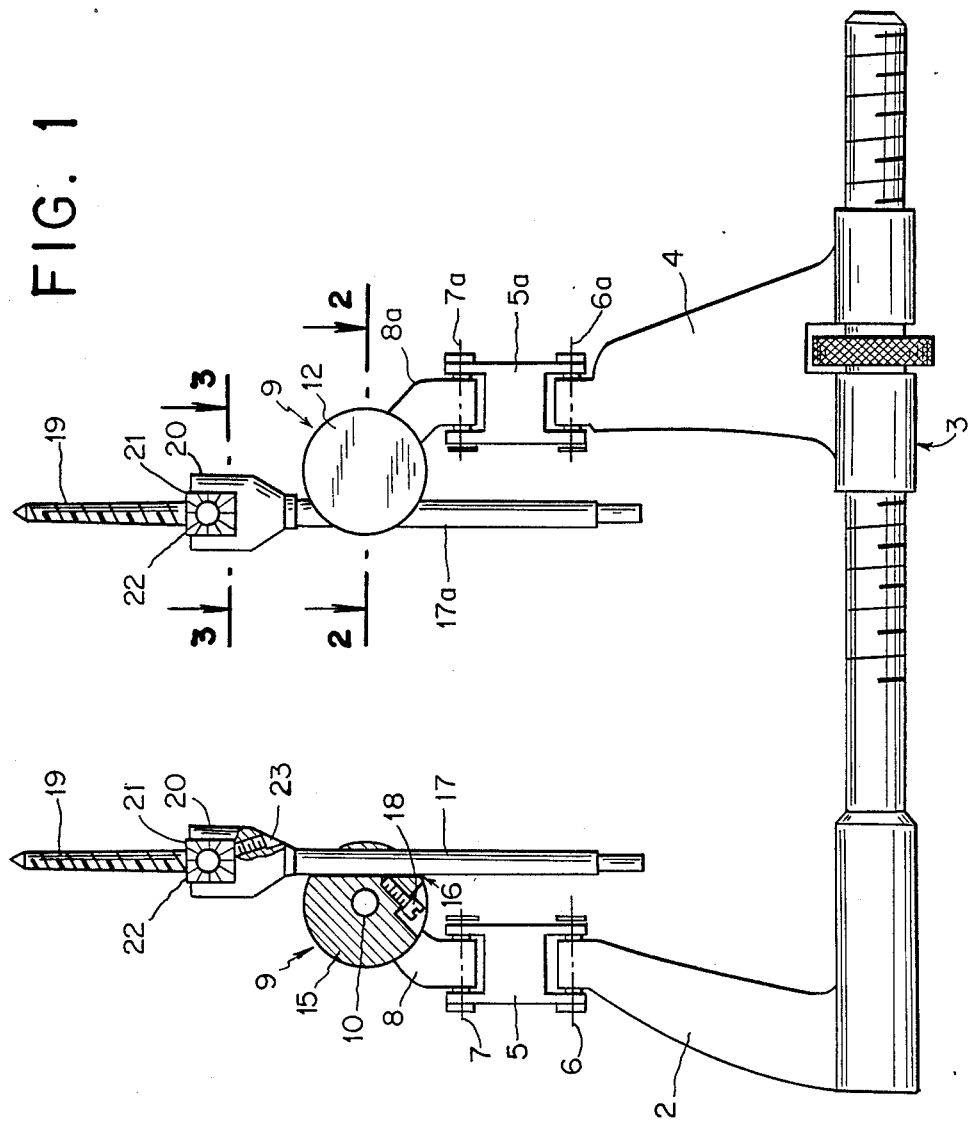

DEVICE FOR SETTING THE SPINAL COLUMN

The invention concerns a device for setting a spinal column with damaged vertebrae, said device consisting of an adjustable arm on a guide shaft and another fixed arm, each of said arms bearing a hollow receiving piece adjustable in two planes for an extension rod which connects to a bone screw.

A device for setting a spinal column with damaged vertebrae is known in which the arms situated on the guide shaft are flexed, said arms bearing threaded pins attached at the end by a hinge, said pins bearing a receiving sheath that can be turned and fastened with a wing nut.

The specific manner in which setting is accomplished, and, in particular, the way the receiving sheath is mounted and fastened down, do not, however, correspond to the requirements which an operator must make on such an instrument, especially with a view toward easy handling.

The purpose of the invention, therefore, is to improve the device for setting a spinal column with damaged vertebrae in such a way as to permit easy handling.

This is achieved in the invention in that each arm has an articulated mid-piece with two hinges, wherein a bracket for the hollow receiving piece is hinged onto the articulated mid-piece, said bracket being in the form of a cylindrical piece with a tangential hole that can be fixed in place.

A setting screw to hold the extension rod in place is mounted at an acute angle to the tangential hole. The cylindrical piece is axially adjustable and can be fixed in an end position.

In an especially advantageous version, the bracket has a perpendicular threaded pin, said pin having a notch plate on one end and at some distance from it a nut which can be turned on the thread, whereby the hollow receiving piece is mounted between the nut and the notch plate in a way that it can be turned and adjusted axially.

The tangential hole 16 receives the extension rod 17. The extension rod 17 is fastened with the set screw 18 which is mounted at an acute angle to the tangential hole 16. The shape of the hollow receiving piece, i.e., as a settable cylindrical piece with a tangential hole makes the device easier to handle, because the parts to be mounted and the parts to be adjusted are readily accessible.

In addition, because of the articulated mid-piece 5 and 5a and the circumstance that the cylindrical piece can be adjusted on the threaded pin 10 the extension piece can be set in any position, so that the extension rods 17 and 17a mounted on the bone screw 19 can also be set accordingly, which effectuates a corresponding setting of the bone screws screwed into the healthy vertebrae.

The special shape of the extension rod and the attached bone screw also represent an improvement in the handling of the device by the operator.

This is achieved in that the extension rod has a recessed configuration 20 which is occupied by the bone screw 19. The bone screw accordingly has a correspondingly shaped profiled piece 21 on its head, with a grid or knurled surface 22 mounted on the top side of said profiled piece 21. The profiled piece 21 is fastened in the recessed configuration 20 by a screw 23 situated at an acute angle to the axis of the extension rod 17 (FIG. 1).

The recessed configuration 20 has a more than semi-circular shape, so that the bone screw 19 with its profiled piece 21 can be longitudinally inserted or withdrawn (FIG. 3).

If the vertebrae 24 are set with this device, this position must be made stationary. This is done with a setting rod 25 made up of the telescoping pieces 26 and 27. The two parts are set by virtue of the circumstance that the inserted part 26 has setting notches 28. The other sleeve-shaped telescoping piece 27 can be firmly fastened to the inserted part in that pressure is exerted with special tongs on the sleeve-shaped telescoping piece in the region of the setting notches, thereby pinching the pieces together. A perforated board, in the shape, for example, of a U-track piece, can serve as an accessory, said board having holes the same distance apart as the setting notches (FIGS. 4 and 5).

The setting rod has on the one end a notch plate 29 provided with a hole, said plate meshing with notchings 22 of the profiled piece 21 if the two parts are connected by a screw 30 (Cf. FIG. 5).

To facilitate the fitting of the screw 30, the screw has a hole 31 in its middle into which a pin bearing a grip (not shown) is inserted. Thus, the screw, seated so to speak, on the grip by means of the pin, can be more easily inserted into the threading.

If the setting rod is in place, the operation is completed, to that the device and the extension rods 17 and 17a can now be taken off.

In the case of short bridging lengths, a one-piece setting rod with one-sided notch plates with a hole can be used. If it is necessary to adjust the mesh plates, which normally are situated in one plane, this can be done by simply rotating the notch plate around the longitudinal axis of the setting rod.

Another version of the extension rod and the bone screw is given in FIGS. 6 and 7. The bone screw 19 has a cylindrical roller 32 onto which an appropriately shaped Y-shaped piece 33 to which the extension rod 17b is connected can be mounted. The front of the roller 32 has notchings or knurled surface 34 to receive the setting rod, as already described. A lug 35 is mounted on the roller so that the roller 32 sits in the Y-shaped piece 33 without turning, said lug fitting into a corresponding recess 36 in the Y-shaped piece.

The drawing presents one version as an example.

FIG. 1 shows the device in side view.

Figure 3:
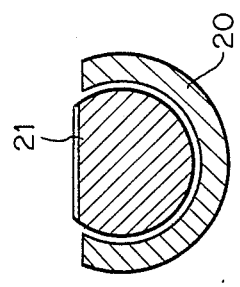
FIG. 3 is a section along the line III—III through the extension rod.

The device for setting a spinal column consists of a guide axis 1 and the arm 2 stationarily mounted on said axis, and the sliding arm 4, which may be adjusted with the threaded spindle 3. Each arm, 2 or 4, bears an articulated mid-piece 5 or 5a, with the hinge axes 6 and 7. A bracket 8 or 8a is hinged to the articulated mid-piece 5 or 5a, said bracket bearing the hollow receiving piece, designated overall as 9. The plane along which the hollow receiving piece is adjusted ia perpendicular to the adjustment plane of the bracket 8 and 8a.

Figure 2:
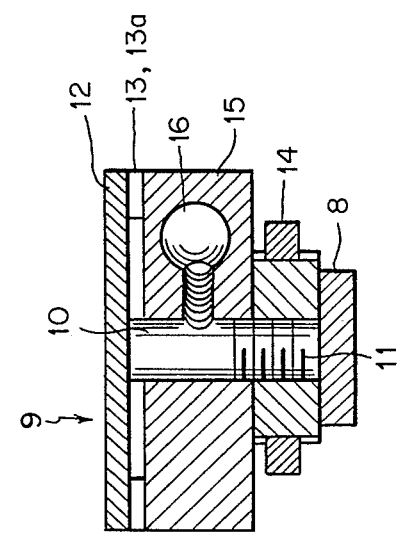
FIG. 2 is a section along the line II—II through the cylindrical piece.
Figure 4:
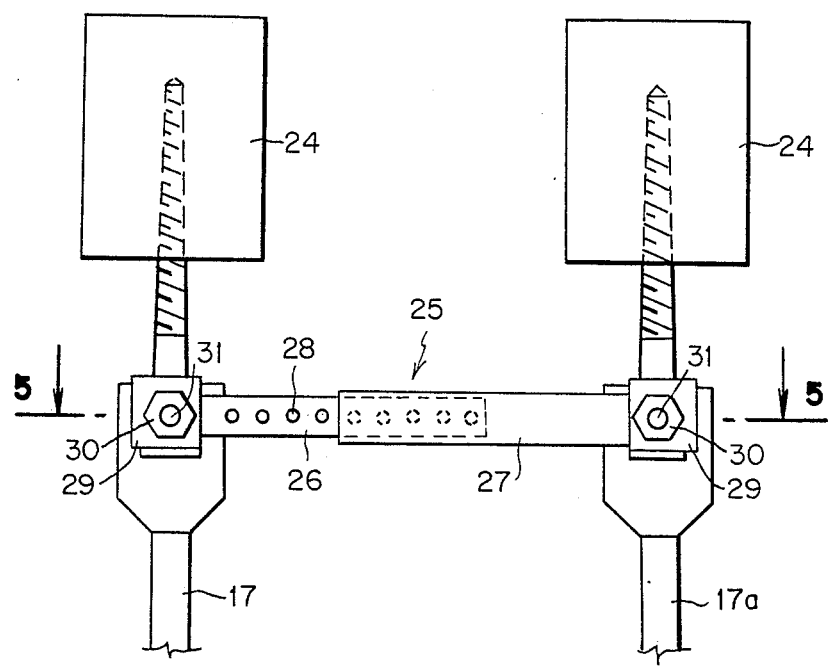
FIG. 4 shows the setting of the bone screws with the aid of a setting rod.
Figure 5:
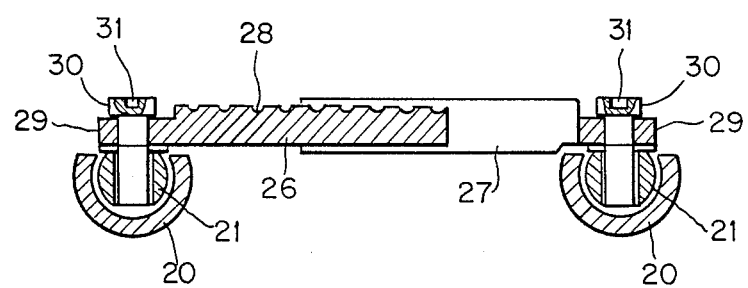
FIG. 5 shows a section along line V—V in FIG. 4.
Figure 7:
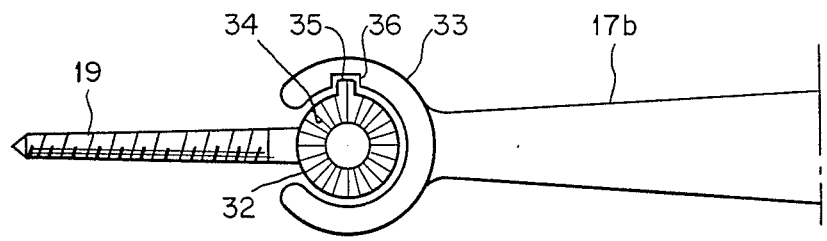
FIG. 6 and FIG. 7 show another version of the bone screws and the extension rod.
Figure 6:
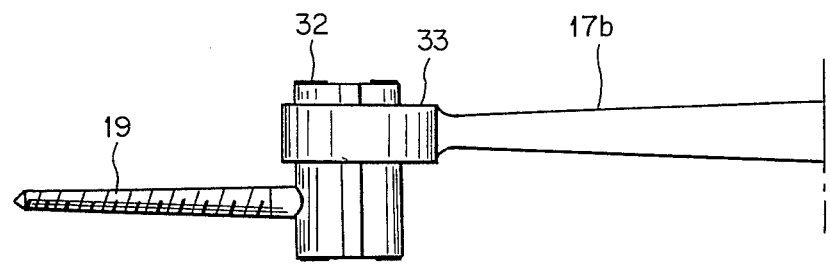

The profile of the hollow receiving device 9 is shown in FIG. 2. A perpendicular threaded pin 10 is firmly mounted on the arm 8, the threading 11 of said pin being on its lower part.

The notch plate 12 is stationarily mounted to the end of the threaded pin, said plate holding the mesh 13. The nut 14 is mounted on the lower end of the threaded pin, i.e., on the threading 11. From this it is clear that the hollow receiving piece, in the form of a cylindrical piece 15, said piece possessing the tangential drill hole 16, is axially adjustable and is set in an end position. Specifically, if the nut 14 is turned, the cylindrical piece 15 moves toward the mesh plate and the mesh on the one side of the mesh plate, namely, the mesh 13 thereby meshing with the mesh 13a on the cylindrical piece.

This makes it possible for the extension rod to be more easily and more accessibly inserted and fixed in the hollow receiving piece in that the cylindrical piece is adjusted axially by means of the nut along with the notch plate, so that the mesh of the mesh plate and the notch of the cylindrical piece mesh together. In addition, the setting screw to fix the extension rod can be more easily manipulated by the operator because of its oblique position. Moreover, the entire device can be more easily positioned through the arrangement of the articulated mid-piece.

Another improvement in the handling of the device is achieved in that the extension rod has a recessed configuration on one end for receiving the bone screw, said screw having an appropriately shaped profiled piece with a notching in the head end for receiving a setting rod. The recessed configuration is more than semicircular in shape, so that the extension rod can be withdrawn only axially.

In this way the extension rod can be mounted on the bone screw in a simple manner because the connection can be accomplished merely by sliding the recessed part onto the corresponding profiled piece.

The bone screw is thus also fastened in the recessed configuration by a screw which is screwed on at an acute angle to the axis of the extension rod, so that in this case too the operator is able to handle the device more easily.

Another possible version of the connection between the bone screw and the extension rod is such that a cylindrical roller is mounted on the bone screw, said piece having a notching for receiving a setting rod, in which case the extension rod then has a Y-shaped piece corresponding to the cylindrical shape on its end such that this extension rod can be slid onto the roller. The extension rod with the roller can be fixed in a stationary position in that, for example, the roller has mounted onto it a lug which fits into a corresponding recess in the Y-shaped piece of the extension rod.

An especially useful version of the setting rod is such that the setting rod consists of telescoping pieces whose inserted part has setting notches, whereby this setting rod also has a notch plate with a hole on its end.

The purpose of this setting rod is to hold the vertebrae set with the aid of the device in the set position so that the damaged part of the vertebral column is bridged over by the setting rod. The length of the setting rod and the relative position of the end mesh plates with regard to one another are then fixed in such a way that the outer telescoping piece is pressed in forming a notch with the aid of appropriately shaped tongs and a perforated board, whereby this notch then fits exactly into the notch of the inserted telescoping piece. For short bridging lengths a one-piece setting rod with a mesh plate with a hole on its end is provided.

I claim:

1. A device for setting a spinal column with damaged vertebrae, said device comprising
   an axial guide member;
   a first arm slideably mounted for axial movement on said guide member;
   a second arm fixedly mounted to said guide member;
   a separate mid-piece hingedly connected to each of said first and second arms;
   a separate bracket hingedly connected to each said mid-piece; and
   a separate hollow receiving piece carried by each bracket and adjustable in two planes for receiving an extension rod adapted for connection to a bone screw, said receiving piece consisting of a cylindrical piece with a central axis having a generally tangential hole therethrough which is transverse to and offset from said central axis and means for fixing the position of said cylindrical piece.

2. The device as defined in claim 1, wherein said cylindrical piece is rotatably adjustable and the means for fixing the position thereof fixed the rotational position of the cylindrical piece.

3. The device as defined in claim 1, which further comprises a set screw mounted at an acute angle to the generally tangential hole in said cylindrical piece so as to intersect said hole and set the position of an extension rod therein.

4. The device as defined in claim 1, wherein the means for fixing the position of said cylindrical piece comprises a threaded pin mounted perpendicularly to each bracket, a nut threadably engaged with said pin, and a stationary notch plate mounted on said pin, said cylindrical piece being rotatably and axially mounted on said pin and disposed between said nut and said stationary notch plate.

5. The device as defined in claim 1, wherein said extension rod has a recess therein at an end adapted for receiving said bone screw, and said bone screw includes a head portion having a correspondingly shaped profile for receipt in said recess with a knurled surface for receiving a setting rod.

6. The device as defined in claim 5, wherein said recess is substantially semi-cylindrical in shape and axially arranged in the end of said extension rod, the substantially semi-cylindrical shape being more than semicircular so that said extension rod can only be withdrawn axially.

7. The device as defined in claim 5, which further includes a set screw in said extension rod arranged at an acute angle to intersect said recess so as to fasten said bone screw head portion therein.

8. The device as defined in claim 1, wherein said bone screw at its connection to said extension rod includes a cylindrical roller having a knurled surface on a front end for receiving a setting rod, said extension rod at its connection to said bone screw includes a Y-shaped piece corresponding to said cylindrical roller for the receipt thereof, and means for preventing said cylindrical roller form turning in said Y-shaped piece.

9. The device as defined in claim 5, wherein said setting rod includes telescoping pieces the male part of which includes setting notches.

10. The device as defined in claim 5, wherein said setting rod is in a single piece.

11. The device as defined in claim 9, wherein said setting rod is formed in one piece with a hole in its end.

12. The device as defined in claim 10, wherein said setting rod is formed in one piece with a hole in its end.

13. The device as defined in claim 5, wherein screw means connects said bone screw to said setting rod, said screw means including a recess in its center for the insertion of a holding pin with a group.

* * * * *

UNITED STATES PATENT AND TRADEMARK OFFICE
CERTIFICATE OF CORRECTION

PATENT NO. : 4,957,495
DATED : September 18, 1990
INVENTOR(S) : Patrick Kluger

It is certified that error appears in the above-identified patent and that said Letters Patent is hereby corrected as shown below:

Cover page, column 1, item 30, line 2, delete "April 1, 1987" and substitute therefor —April 2, 1987—.

Signed and Sealed this

Twenty-seventh Day of November, 1990

*Attest:*

HARRY F. MANBECK, JR.

*Attesting Officer*      *Commissioner of Patents and Trademarks*